United States Patent [19]

Martino et al.

[11] Patent Number: 5,021,238
[45] Date of Patent: Jun. 4, 1991

[54] WATER-BASED TWO-PHASE AEROSOL HAIRSPRAYS

[75] Inventors: Gary T. Martino, Plainsboro; Frank A. Nowak, Jr., Somerville, both of N.J.

[73] Assignee: National Starch and Chemical Investment Holding Corporation, Wilmington, Del.

[21] Appl. No.: 408,659

[22] Filed: Sep. 18, 1989

[51] Int. Cl.$^5$ .............................................. A61K 7/11
[52] U.S. Cl. ...................................... 424/47; 424/81; 424/DIG. 1; 424/DIG. 2
[58] Field of Search .................... 424/47, 81, DIG. 1, 424/DIG. 2

[56] References Cited

U.S. PATENT DOCUMENTS

| | | | |
|---|---|---|---|
| 2,996,471 | 8/1961 | Reiter et al. | 260/33.4 |
| 3,137,416 | 6/1964 | Shepherd et al. | 222/394 |
| 3,207,386 | 9/1965 | Presant et al. | 222/394 |
| 3,405,084 | 10/1968 | Bohac et al. | 260/29.6 |
| 3,445,566 | 5/1969 | Skoultchi et al. | 424/47 |
| 3,577,517 | 5/1971 | Kubot et al. | 424/47 |
| 3,810,977 | 5/1974 | Levine et al. | 424/47 |
| 3,927,199 | 12/1975 | Micchelli et al. | 424/47 |
| 3,984,536 | 10/1976 | Viout et al. | 424/47 |
| 4,192,861 | 3/1980 | Micchelli et al. | 424/47 |
| 4,719,099 | 1/1988 | Grollier et al. | 424/47 |
| 4,842,852 | 6/1989 | Nowak, Jr. et al. | 424/71 |
| 4,859,455 | 8/1989 | Nowak, Jr. et al. | 424/47 |
| 4,874,604 | 10/1989 | Sramek | 424/47 |
| 4,923,695 | 5/1990 | Nowak, Jr. et al. | 424/71 |
| 4,933,170 | 6/1990 | Nowak, Jr. et al. | 424/47 |

FOREIGN PATENT DOCUMENTS 1192135 8/1981 Canada .
0260641 3/1988 European Pat. Off. .

OTHER PUBLICATIONS

Petter et al., Kosmetika Aerosole Reichstoff, pp. 427-430, Aug. 30, 1987.
Vogel, G. M., New Hair Care Polymers, Cosmetics & Toiletries, 100, pp. 43-51 (4/85).
Koehler, F. T., Carboxylated Resin Systems in Hair Care Products, Cosmetics & Toiletries, 94, pp. 75-76 (4/79).

*Primary Examiner*—Thurman Page
*Assistant Examiner*—Robert H. Harrison
*Attorney, Agent, or Firm*—Edwin M. Szala; Royal N. Ronning, Jr.

[57] ABSTRACT

This invention presents novel two-phase hair-fixing aerosol systems which are aqueous-based. The systems, which utilize dimethyl ether as a propellant (and also a solvent, as needed), can be shaken to form a semi-stable emulsion or mixture which is stable for a time sufficient for spraying, and are compatible with a wide variety of hair-fixing resins.

9 Claims, No Drawings

WATER-BASED TWO-PHASE AEROSOL HAIRSPRAYS

BACKGROUND OF INVENTION

For some time, use of aerosol spray systems have been utilized to provide easy, rapid delivery of hair-fixing compositions to the surface of the hair. Ordinarily, such systems consist of a single-phase which comprises a solvent (usually an alcohol) which is capable of dissolving both the hair-fixing composition and the aerosol propellant (which is usually a hydrocarbon or a halogenated hydrocarbon having a high vapor pressure). These single-phase systems deliver a fairly uniform amount of composition in the spray until the contents of the container are exhausted.

However, the environmental consciousness of the international community is increasing the use of such propellants is becoming much less desirable. Additionally, the popularity of alcohol in hairsprays is declining among the consumer population due to the perception that it dries out the hair, making it brittle and easily damaged.

Because of these and other reasons, researchers have attempted to utilize water as the sole solvent in aerosol hairsprays. For example, U.S. Pat. No. 3,207,386 discloses a single-phase aqueous system which utilizes dimethyl ether as the propellant. However, this system suffers from the distinct drawback of requiring the amounts of resin, water, and propellant to fall within narrow limits of solubility to form a usable spray.

Use of a two-phase (solvent and propellant) system was disclosed in U.S. Pat. No. 3,137,416, wherein the propellant is used to force an aqueous or water/alcohol solution of hairspray resin through a dip tube to form the spray, resulting in a very wet spray. This system suffers from the drawback of having to use a large quantity of propellant, as well as the fact that only water (or water/alcohol) soluble resins can be used. Also, according to the patent, mixing of the propellant and aqueous phases is to be avoided; thus, the containers must be handled very carefully prior to use.

A number of researchers have also attempted to make single-phase aqueous systems by including organic cosolvents with the water. These cosolvents, which are usually alcohols, are often employed in very large amounts, generally exceeding 30%, making them a substantial component in the hairspray systems. It follows that these systems suffer from the same drawbacks as alcohol or organic solvent systems.

Thus, there exists a real need for aqueous based-systems which exhibit a wide versatility with regard to resins which can be used, relative proportions of each component, and lack the requirement of an organic cosolvent.

SUMMARY OF INVENTION

This invention relates to two-phase, aqueous-based systems for the aerosol delivery, of hair-fixing compositions as an atomized spray. These systems, which utilize dimethyl ether (DME) as the propellant (as well as a solvent in some cases), possess the desirable properties of using water as the only solvent, possess a wide range of resins which can be incorporated, and demonstrate a similar versatility with regard to the relative proportion of each component. Thus, the sprays can be made very wet (wherein the amount of resin and DME is low compared to the amount of water) or dry (wherein the amount of resin and DME is high compared to the amount of water) as the particular applications require.

Additionally, the versatility of these two-phase systems with regard to choice of resin is very wide, due to the fact that two separate liquid phases (water and DME) of different polarity are employed. Thus, the less polar resins will be preferentially dissolved in the phase which is predominantly DME, while the more polar resins will be preferentially dissolved in the predominantly aqueous phase. If mixtures of both polar and non-polar resins are employed, the separate components can dissolve in either phase, thus permitting the entire mixture to be dissolved.

The two-phase systems of this invention are shaken immediately prior to use, and form a semi-stable emulsion or mixture. This emulsion must be stable for a time sufficiently long to permit application of the spray to the hair, generally at least 10 seconds, more preferably 30 seconds, most preferably 1 minute, but this time will vary as particular applications dictate.

DETAILED DESCRIPTION OF INVENTION

The two-phase aerosol systems of this invention comprise dimethyl ether (primarily as a propellant but also as a solvent in some cases), water as a solvent, and one or more hair-fixing resins. The resins may be soluble in either the DME, water, or both.

The proportions of each component will vary as the particular requirements of specific applications dictate, with relatively larger quantities of water being utilized when wetter sprays are desired, and smaller quantities of water being utilized when drier sprays are desired. Regardless of the degree of wetness or dryness, however, the ratio of DME/water (wt/wt) must exceed 0.5/1.0, the solubility limit of DME in water. Above this value, two distinct phases, predominantly aqueous and predominantly DME, are formed, while below it, the system is single-phase.

The benefit of the two-phase system, in addition to its versatility in the degree of spray wetness or dryness, is that a wide variety of resins can be used. Essentially, any resin exhibiting solubility in DME or water, or both, can be employed. Further, mixtures of resins of different polarities can be used, since the less polar components will tend to dissolve in the phase which is predominantly DME, while the more polar components will dissolve in the phase which is predominantly water.

It is, thus, anticipated that the two-phase systems of this invention can be used with virtually any hair-fixing resin ordinarily amenable to spray applications, the only criterion being the resin's solubility in at least one of the phases. Such resins can be utilized in neat form or, if they possess acid functionalities, can be partially or completely neutralized by alkaline agents as those described in U.S. Pat. Nos. 2,966,471, 3,405,084, 3,577,517, 4,192 861, and 4,842,852, all of which are incorporated herein by reference. Such agents include organic and inorganic bases such as 2-amino-2-methyl-1-propanol (abbreviated as AMP) and KOH or NaOH.

It is also anticipated that the DME propellant may, for economic reasons, be blended with small amounts of hydrocarbon propellants. The amount of these hydrocarbons, however, should be kept low to avoid the formation of a third phase or undesirable foaming. Suitable hydrocarbons include the lower molecular weight ($C_5$ and lower) alkanes and alkenes, such as butane, propane, and ethylene.

Other additives normally found in aerosol hairsprays, e.g. surfactants, perfumes, etc., can also be added to the systems, so long as they are soluble in at least one of the phases.

The precise quantity of resin (or of each component in the resin mixture) used will depend upon the amount needed for the desired application, as well as its solubility in the DME and/or water. Each particular resin or resin mixture will exhibit discrete limits outside of which the resin is not soluble, the exact value limits depending upon the nature of the other resins (if any) present, the ratio of DME/water, and the specific solubility of that resin in DME, water, or both. Further, the resin must be present in an amount such that it will exhibit satisfactory hair-fixing properties when applied (generally 0.5% by weight or greater although this will vary from resin to resin).

Additionally, the two-phases of the aerosol-based systems of the instant invention must form a semi-stable emulsion or mixture when shaken prior to use. The semi-stable single-phase emulsion or mixture thus formed permits more propellant to be actuated with the aerosol spray, thus providing a drier spray possessing shorter drying times than the conventional water based system of the prior art. While the time required for this stability will, of course, vary in different applications, in general the phase should be stable for at least 10 seconds. Preferably, the emulsion should remain stable for a longer time, at least 30 seconds more preferably at least 1 minute, to permit versatility in spray time.

The aerosol sprays thus formed will provide a convenient method whereby uniform quantities of resin can be applied directly to the hair.

EXAMPLES

The following examples illustrate specific embodiments of the inventions, but are not intended to be illustrative of all embodiments.

EXAMPLE 1 - HAIRSPRAY RESINS

A series of different hairspray resins were formulated or purchased commercially for examination in the two-phase systems of the invention. The resins had the following compositions.

| Sample | Resin Trade Names [Supplier] | CTFA Designations |
|---|---|---|
| A | Amphomer ® [NSC]* | Octylacrylamide/acrylates/butylaminoethyl methacrylate copolymer |
| B | Resyn ® 28-1310 [NSC] | Vinyl acetate/crotonic acid copolymer |
| C | Resyn ® 28-2930 [NSC] | Vinyl acetate/crotonic acid/vinyl neodecanoate copolymer |
| C¹ | Resyn ® 28-2913 [NSC] | Vinyl acetate/crotonic acid/vinyl neodecanoate copolymer |
| D | Versatyl ™ 40 [NSC] | Octylacrylamide/acrylates copolymer |
| E | Versatyl ™ 42 [NSC] | Octylacrylamide/acrylates copolymer |
| F | Experimental Resin [NSC] | Vinyl acetate/vinyl neodecanoate/maleic half-ester |
| G | Ultrahold-8 [BASF] | Acrylate/acrylamide copolymer |
| H | Luviset CAP [BASF] | Vinyl acetate/crotonic acid/vinyl propionate copolymer |
| I | PVP K-30 [GAF] | PVP |
| J | PVP/VA E-335 [GAF] | PVP/Vinyl acetate copolymer |
| K | PVP/VA E-735 [GAF] | PVP/Vinyl acetate copolymer |
| L | Gantrez ES-225 [GAF] | Ethyl ester of PVM/MA copolymer |
| M | Gantrez ES-425 [GAF] | Butyl ester of PVM/MA copolymer |
| N | Gaffix VC-713 [GAF] | Vinyl caprolactam/PVP/dimethyl aminoethyl methacrylate copolymer |

*NSC = National Starch and Chemical Corporation.

EXAMPLE 2 - TWO-PHASE AEROSOL SYSTEMS

Each of the above resins was examined for the resin solubility limit and the water and DME upper and lower solubility limits using the following procedures.

RESIN SOLUBILITY LIMIT

The solubility limit of each resin was determined by preparing a series of two-phase formulations employing differing concentrations of the resin. Specifically, the desired quantities of resin and water were mixed and subsequently neutralized (to 90% or to manufacturer's recommendations) with AMP. The neutralized mixture was then transferred to a pressure bottle equipped with a spray valve, and a total of 40% (by wt) of DME was charged.

Each bottle was shaken gently and observed for precipitation of the resin. If no precipitation was observed, the bottle was again shaken and the spray was initiated. The spray was observed for presence of foaming at a distance of 10-inches from the valve. The resin concentration at which either precipitation or undesirable foaming was observed is listed as the resin solubility limit.

UPPER/LOWER SOLUBILITY LIMITS OF DME AND WATER

The upper and lower limits of DME and water were determined at a constant resin concentration of 4% (not including the weight of the neutralizing agent), a concentration at or below the solubility limit of all resins examined. Determinations were made using the same procedures as for the resin solubility limits.

Specifically, a series of two phase formulations are made, at a 4% resin concentration, where the amount of the component being examined (water or DME) is varied. The lowest concentration of that component at which a stable system (i.e., no precipitate or foaming) is formed is its lower limit while the highest concentration is its upper limit. These results are reported both for water and DME.

The results of these determinations are summarized below.

| Sample | Solub. Limit Resin (wt %) | Upper/Lower limits (wt %) | |
|---|---|---|---|
| | | Water | DME |
| A | 5 | 60/10 | 86/36 |
| B | 6 | 63/13 | 83/33 |
| C | 7 | 56/8 | 88/40 |
| C¹ | 7 | 56/8 | 88/40 |
| D | 6 | 57/35 | 61/39 |
| E | 6 | 57/35 | 61/39 |
| F | 6 | 60/20 | 76/36 |
| G | 6 | 69/10 | 86/27 |
| H | 6 | 77/10 | 86/19 |
| I | 14 | 61/8 | 88/35 |
| J | 5 | 77/19 | 77/19 |
| K | 5 | 59/16 | 80/37 |

-continued

| Sample | Solub. Limit Resin (wt %) | Upper/Lower limits (wt %) | |
| --- | --- | --- | --- |
| | | Water | DME |
| L | 5 | 58/9 | 87/38 |
| M | 5 | 38/9 | 87/58 |
| N | 4 | 61/13 | 83/35 |

As shown, it can be seen that the water-based sprays of this system exhibit a wide versatility to the resin type, as well as to the limits of DME and $H_2O$ to form stable sprays.

It is apparent that many modifications and variations of this invention as hereinabove set forth may be made without departing from the spirit and scope thereof. The specific embodiments described are given by way of example only and the invention is limited only by the terms of the appended claims.

What is claimed is:

1. In an aerosol hair-fixing composition which comprises one or more hair-fixing resins, water, and dimethyl ether, the improvement consisting essentially of
   (i) using the dimethyl ether and water in a ratio greater than 0.5/1 (wt/wt) such that two liquid phases are present, and
   (ii) employing an effective amount of hair-fixing resin, such that no precipitated resin is present, and characterized in that the two liquid phases, when shaken, form an emulsion which does not separate for at least 10 seconds.

2. The aerosol hair-fixing composition of claim 1, wherein the hair-fixing resins include both polar and non-polar resins.

3. The aerosol hair-fixing composition of claim 1, wherein the hair-fixing resins are partially or completely neutralized by a base.

4. The aerosol hair-fixing composition of claim 3, wherein the base is an organic base.

5. The aerosol hair-fixing composition of claim 4, wherein the organic base is 2-amino-2-methyl-1-propanol.

6. The hair-fixing composition of claim 3, wherein the base is an inorganic base.

7. The aerosol hair-fixing composition of claim 6, wherein the inorganic base is KOH or NaOH.

8. The aerosol hair-fixing composition of claim 1, wherein the resin is a copolymer of vinyl acetate and crotonic acid.

9. The aerosol hair-fixing composition of claim 1, wherein the resin is a copolymer of vinyl acetate, crotonic acid, and vinyl neodecanoate.

* * * * *